United States Patent
Maezono et al.

(10) Patent No.: US 6,930,772 B2
(45) Date of Patent: Aug. 16, 2005

(54) METHOD AND DEVICE FOR INSPECTING DEFECT OF SHEET-SHAPED TRANSPARENT BODY

(75) Inventors: Shinji Maezono, Osaka (JP); Satoshi Kanki, Osaka (JP)

(73) Assignee: Nippon Sheet Glass Company, Limited, Tokyo (JP)

( * ) Notice: Subject to any disclaimer, the term of this patent is extended or adjusted under 35 U.S.C. 154(b) by 132 days.

(21) Appl. No.: 10/473,442

(22) PCT Filed: Jul. 3, 2002

(86) PCT No.: PCT/JP02/06720

§ 371 (c)(1),
(2), (4) Date: Sep. 26, 2003

(87) PCT Pub. No.: WO03/005007

PCT Pub. Date: Jan. 16, 2003

(65) Prior Publication Data

US 2004/0179193 A1 Sep. 16, 2004

(30) Foreign Application Priority Data

Jul. 5, 2001 (JP) ....................... 2001-204571

(51) Int. Cl.⁷ ............................ G01N 1/10; G01N 21/84
(52) U.S. Cl. .................................... 356/239.1; 356/429
(58) Field of Search .......................... 356/239.1–239.3, 356/429–431, 237.1, 237.2, 237.3; 250/562, 563, 572

(56) References Cited

U.S. PATENT DOCUMENTS

| | | | | |
|---|---|---|---|---|
| 5,018,867 A | * | 5/1991 | Piironen | 356/445 |
| 5,243,402 A | * | 9/1993 | Weber et al. | 356/429 |
| 5,452,079 A | * | 9/1995 | Okugawa | 356/239.1 |
| 5,691,811 A | * | 11/1997 | Kihira | 356/239.1 |
| 5,870,204 A | * | 2/1999 | Chiu et al. | 356/430 |
| 6,392,754 B1 | * | 5/2002 | Pingel et al. | 356/603 |
| 6,570,651 B1 | * | 5/2003 | Haubold et al. | 356/239.1 |
| 2004/0066502 A1 | * | 4/2004 | Ohtsu | 356/32 |

FOREIGN PATENT DOCUMENTS

| | | |
|---|---|---|
| JP | 8-128968 A | 5/1996 |
| JP | 8-178855 A | 7/1996 |
| JP | 8-220021 A | 8/1996 |

OTHER PUBLICATIONS

Laguesse, Michel F. "Optical Detection and Localization of Holes in Strips Using a Fluorescent Fiber Sensor" IEEE Transactions on Instrumentation and Measurement, vol. 39, No. 1, Feb. 1990.*
International Search Report, Sep. 10, 2002.

* cited by examiner

Primary Examiner—Michael P. Stafira
(74) Attorney, Agent, or Firm—RatnerPrestia

(57) ABSTRACT

A method for detecting a flaw accompanied with an optical defect if any on or in a sheet-like transparent body which is moved, and determine its type comprises placing an illuminator on one side of a sheet-like transparent body, and placing a (one-dimensional) image pickup on the opposite side. The illuminator means comprises lighting and darkening portions, and the image pickup is placed relative to the illuminator such that the boundary between the portions appears on the image pickup as a straight line in parallel with the long axis of the pickup. Image data created from the image pickup, are subjected to contrast enhancement to provide contrast enhanced image data which are displayed as a contrast enhanced image. The sequence (flaw pattern) of light spots and dark spots appears in the enhanced image as of the sheet-like transparent body is moved, and determines the type of flaw.

8 Claims, 15 Drawing Sheets

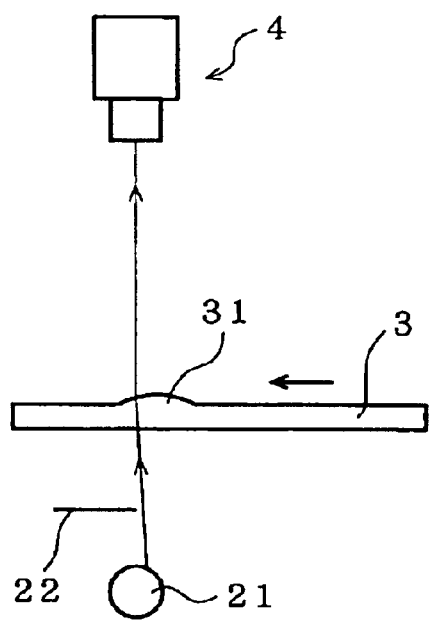
F I G. 4 A
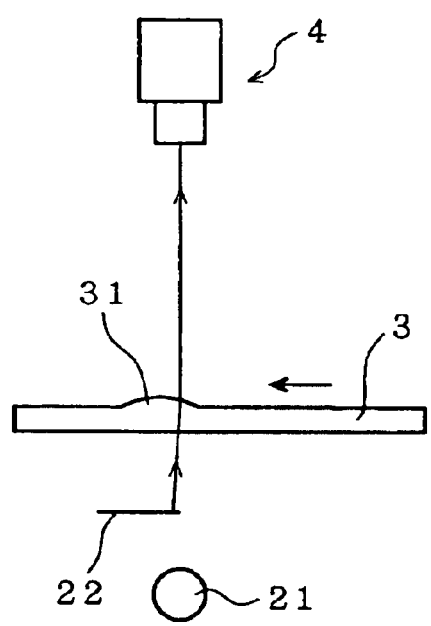
F I G. 4 B
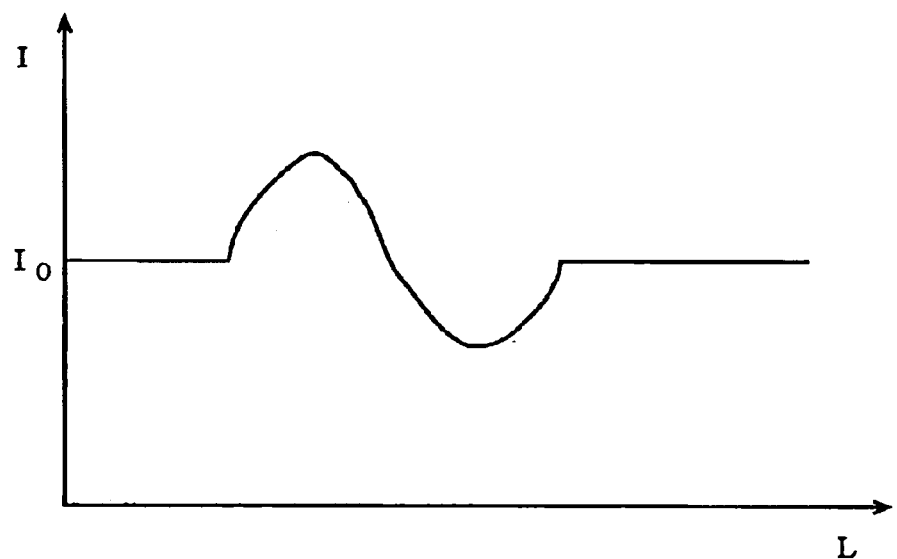
F I G. 4 C

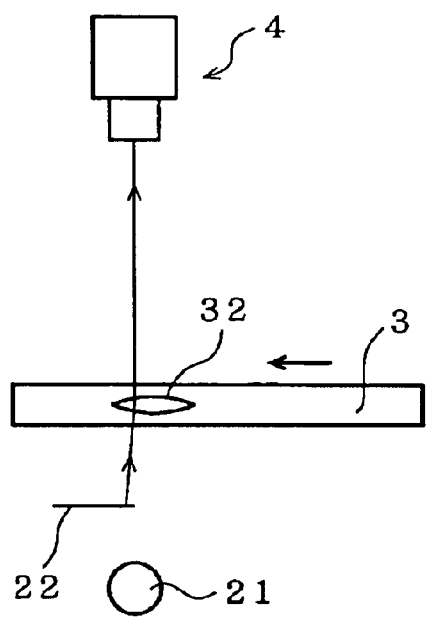
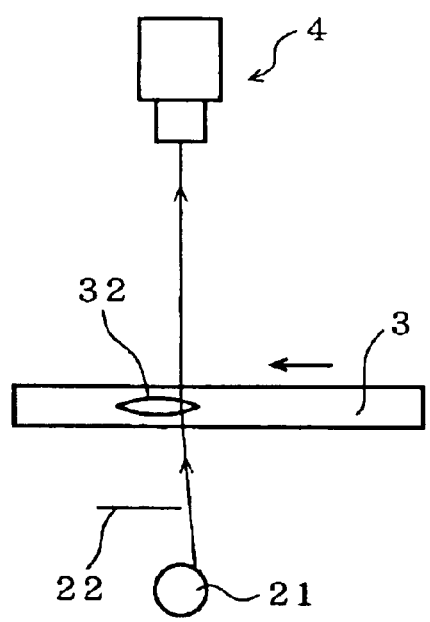
F I G. 5 A    F I G. 5 B
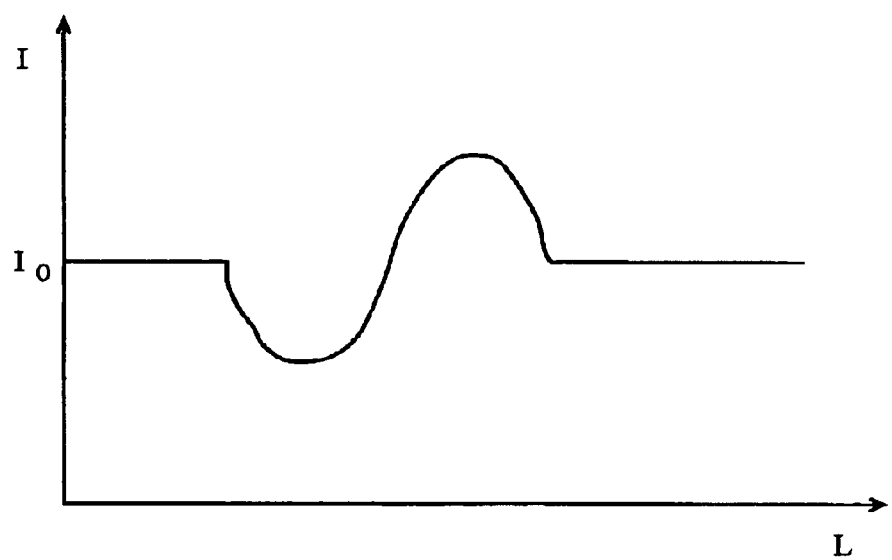
F I G. 5 C

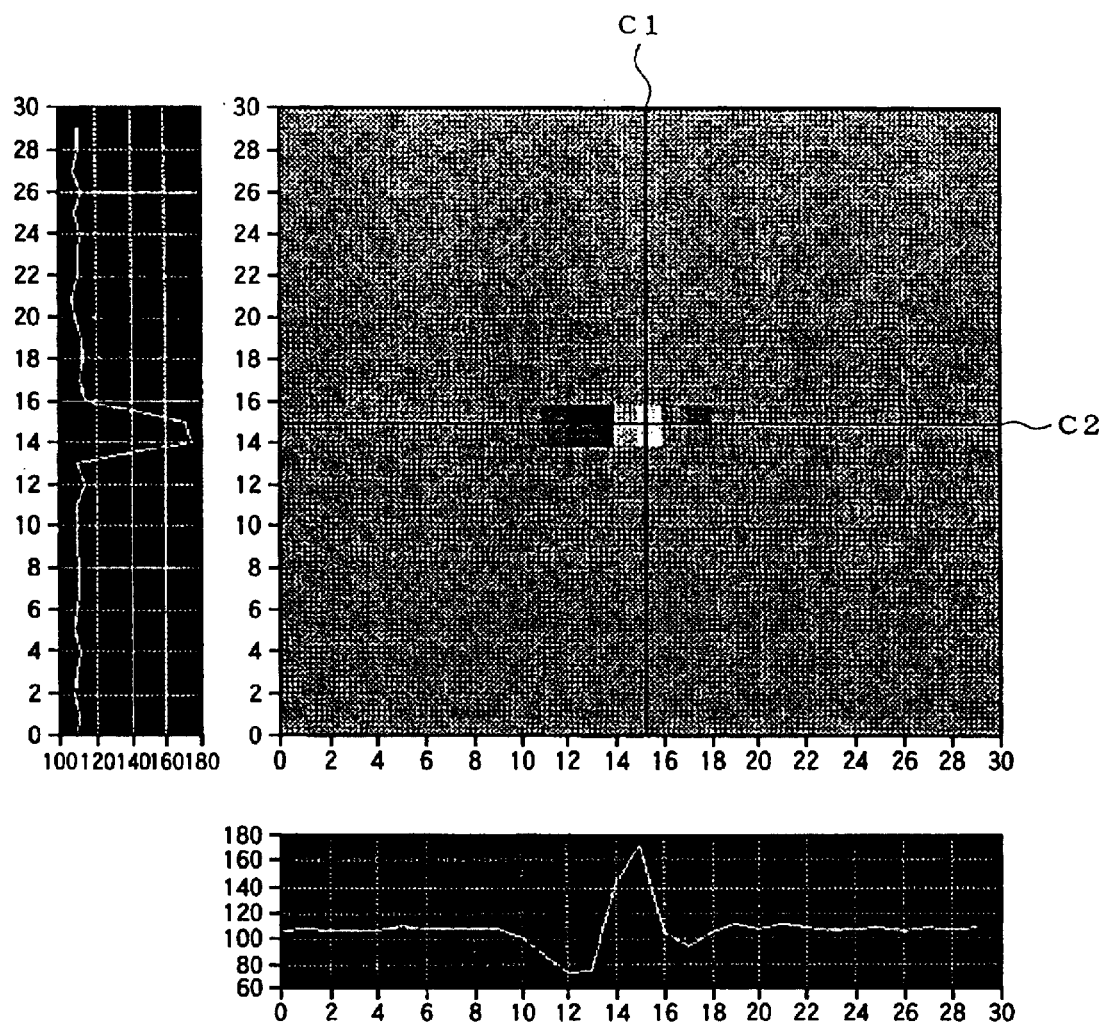
F I G. 6

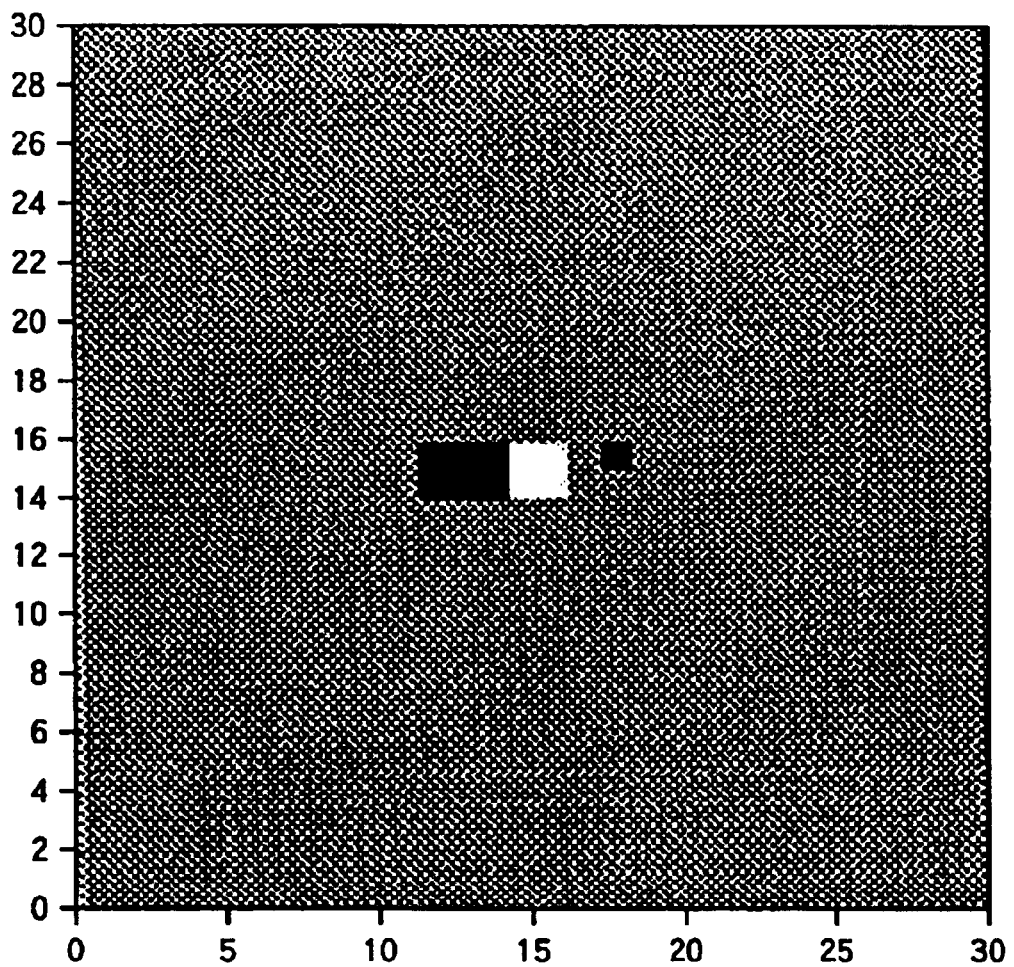
F I G. 7

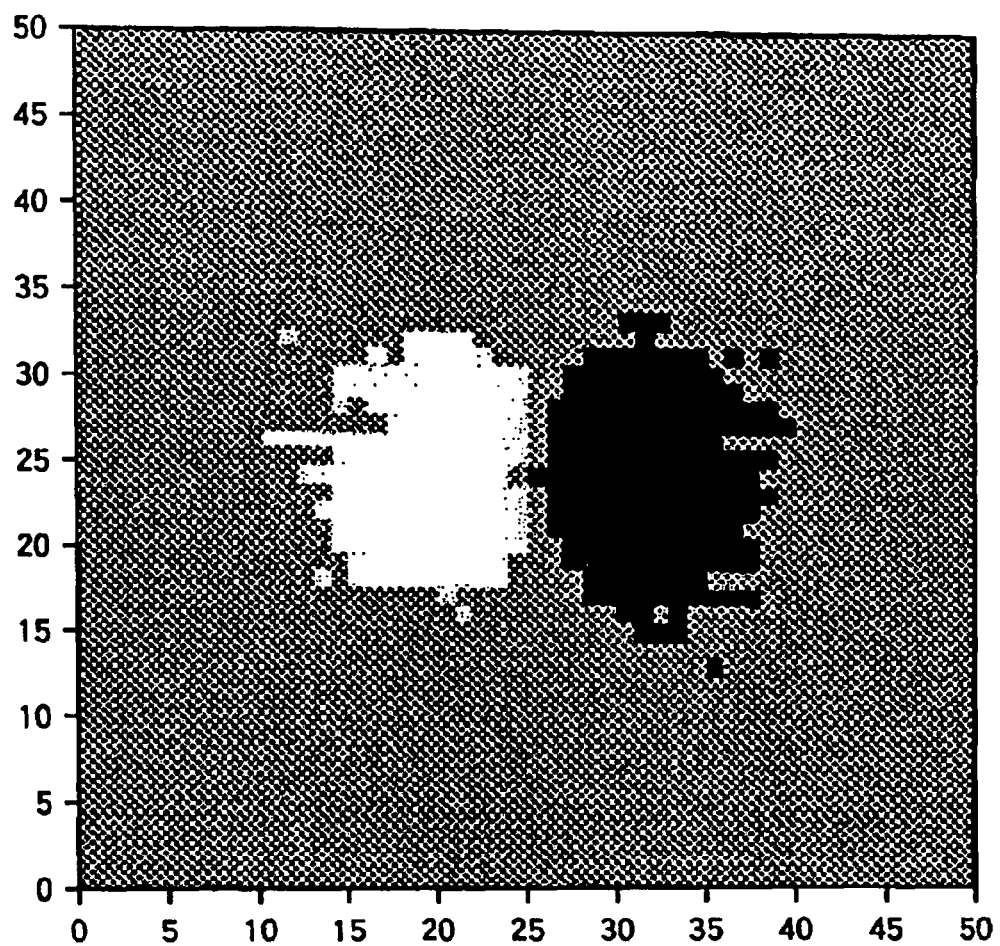
F I G. 9

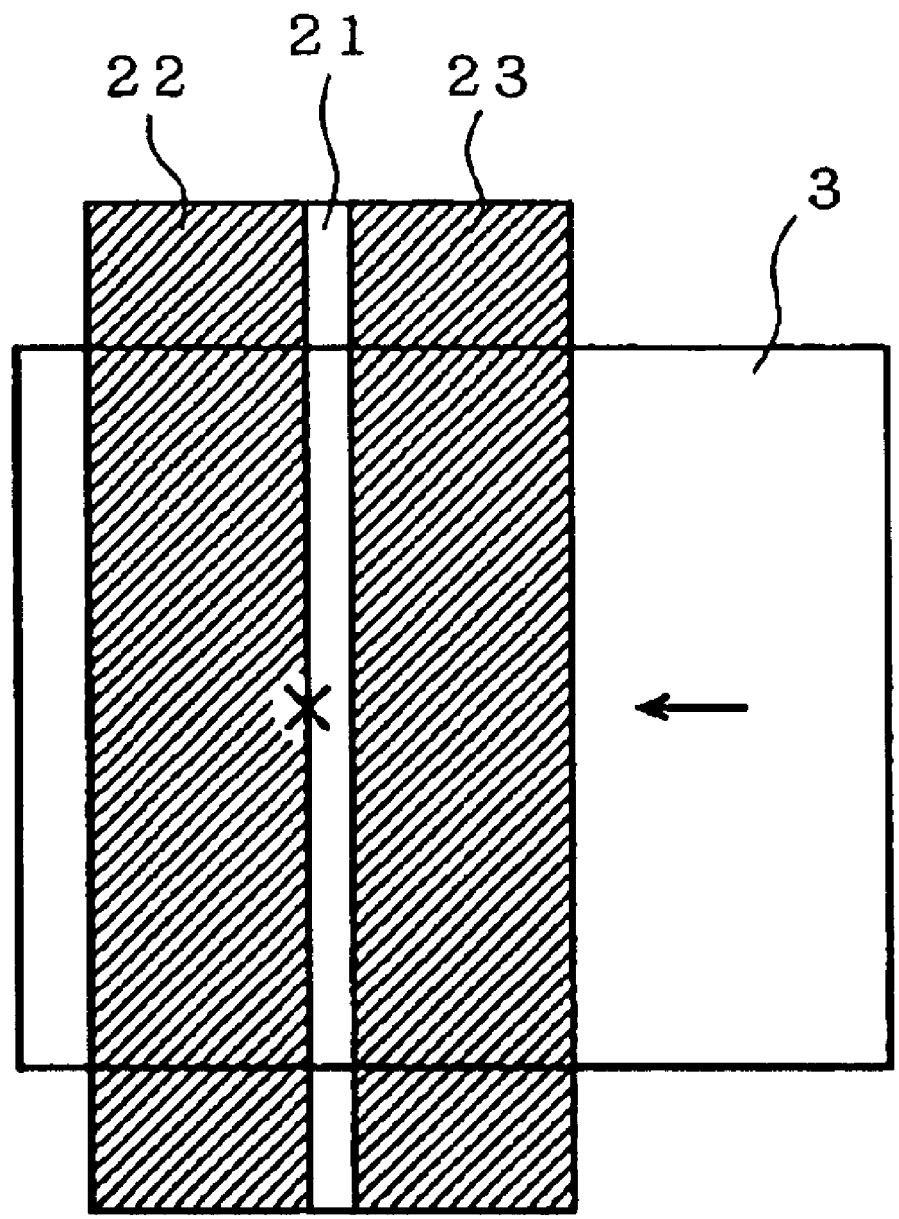
F I G. 1 1

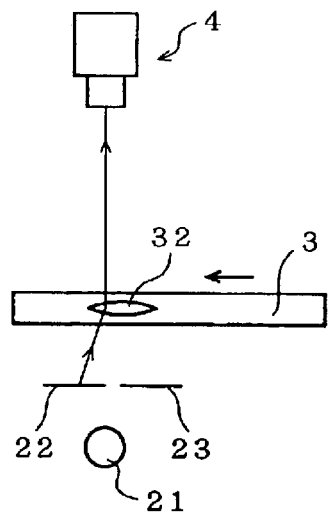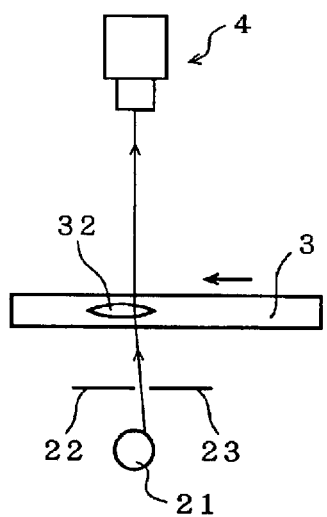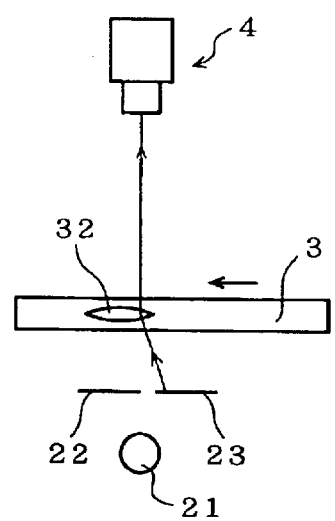
FIG.12A   FIG.12B   FIG.12C
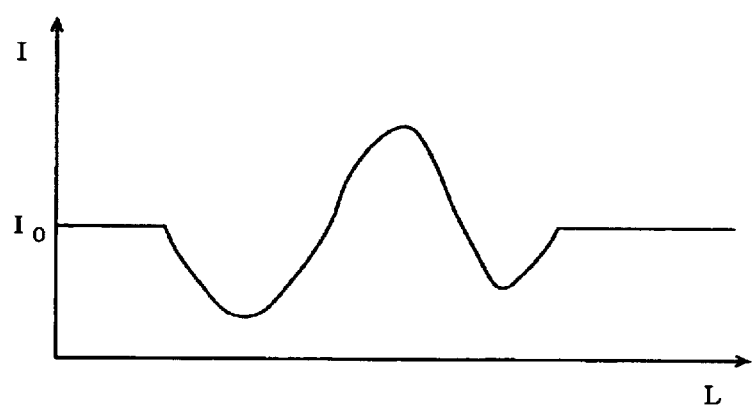
FIG.12D

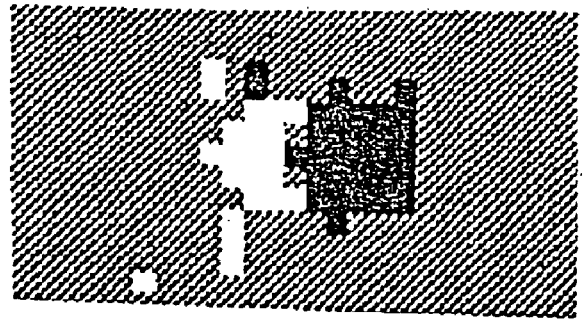
F I G. 1 4 A
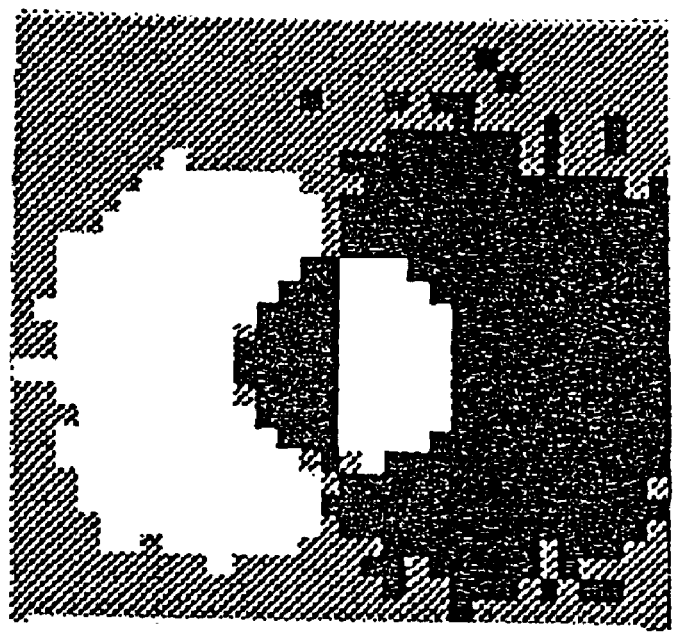
F I G. 1 4 B

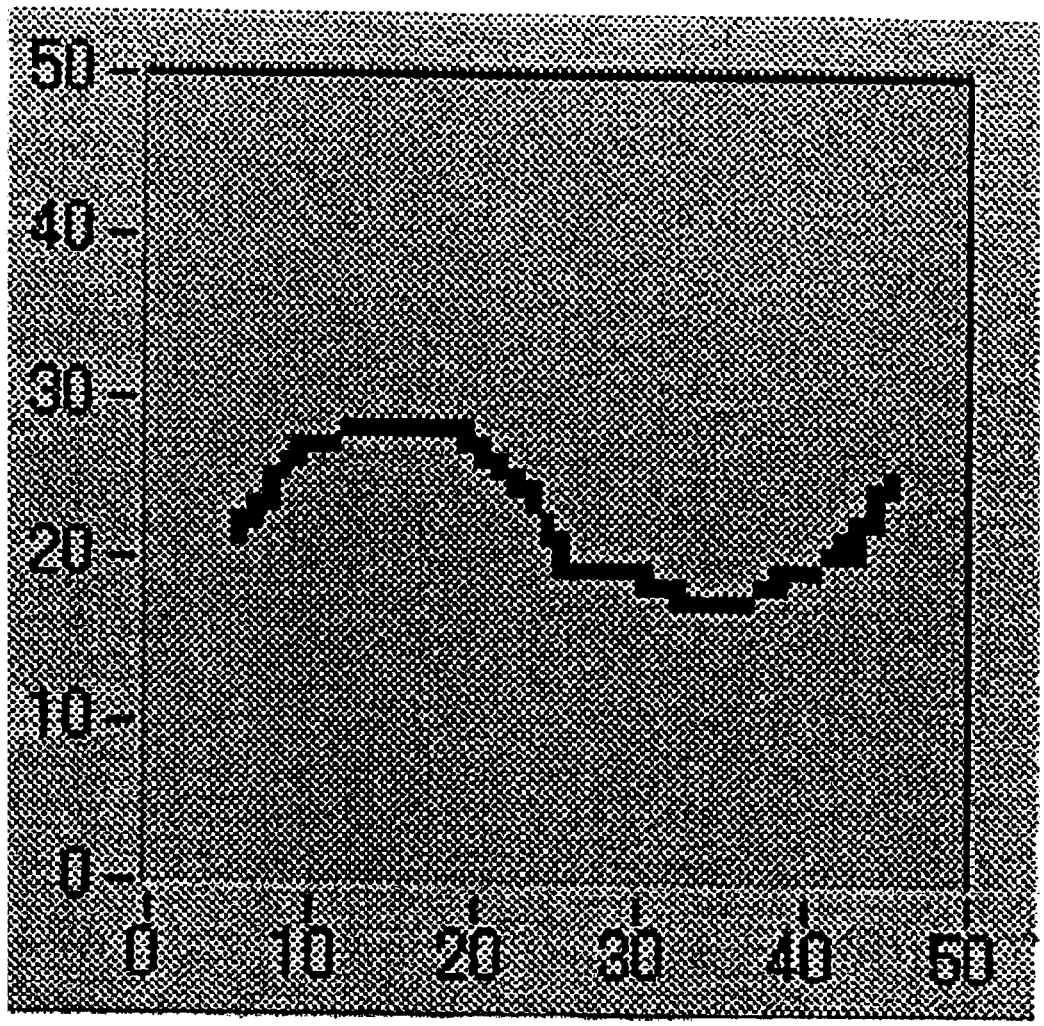
F I G. 1 5

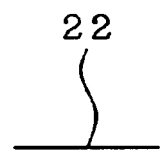
FIG. 16
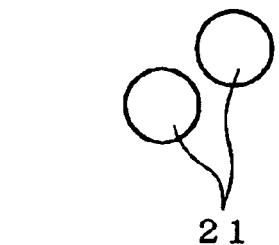
FIG. 17
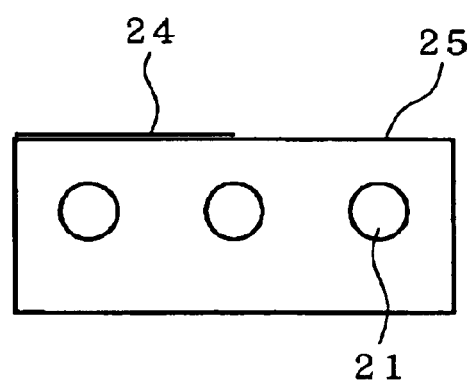
FIG. 18
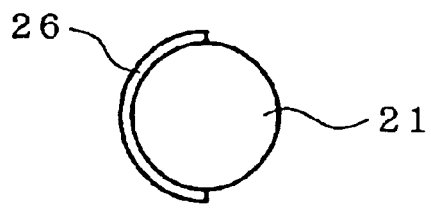

METHOD AND DEVICE FOR INSPECTING DEFECT OF SHEET-SHAPED TRANSPARENT BODY

TECHNICAL FIELD

The present invention relates to a testing method for detecting a flaw accompanied with an optical defect in a sheet-like transparent body such as a transparent plate like a glass plate, or a transparent plate coated with a transparent film, and a testing system for detecting such a flaw.

BACKGROUND ART

The flaw which may be present in a transparent plate such as a glass plate includes indentations which may exist on the surface, foreign objects falling from above, and resting on and adhering to the surface, a crater-like pit and edge left by such a falling foreign object, and a foreign object and air bubble entrapped in the glass body. If the transparent plate is a glass plate whose surface is coated with a transparent film, the flaw may include a pinhole on the surface. If the flaw is accompanied with an optical defect, light incident upon the surface damaged with the flaw is abnormally refracted. A glass plate having any flaw accompanied with an optical defect must be identified via test to be rejected because such a plate is not utilizable as an optical substrate.

A testing method for detecting an optical defect of a glass plate is disclosed in the Japanese Patent Publication No. 8-247954. The testing method described in this publication consists of changing the position of a test object with respect to a light source and an image recording device, allowing the test object to pass behind a boundary edge between a light scattering portion and a light shielding portion, comparing image data acquired before the object passes behind the boundary edge and image data acquired after the object has passed behind the boundary edge, and detecting an optical defect if any based on an absolute value of the difference between the two data. However, according to this method of detecting an optical defect based on an absolute value of the difference between the two image data, one acquired before the object passes behind the boundary edge and the other acquired after the object has passed behind the boundary edge, it will not be possible to distinguish different kinds of flaws accompanied with an optical defect from one another, e.g., between a foreign object and an air bubble both entrapped in a glass plate.

Another method disclosed in the Japanese Patent No. 3178644 (U.S. Pat. No. 5691811A and EP 0726457A2) consists of allowing light from a light source to pass through a mesh structure placed close to the light source where plural thin light shielding septa and light transmitting slits repeat themselves alternately, and to impinge on a test transparent plate and penetrate the test plate, and allowing then a linearly extended camera placed opposite to the light source with the test transparent plate in between to receive light carrying an image consisting of a stripe of dark and light bars, which then transmits the image to an image processing unit so that a flaw if any in the test transparent plate can be detected through the analysis of the image. According to this method, detection of a flaw accompanied with an optical defect as distinct from a simple blemish such as a dust or soil adhered on the surface is achieved by displacing the focus of the camera apart from the mesh structure such that the black (dark) bars corresponding with the septa and white (light) bars corresponding with the slits constituting the stripe overlap with each other to give a grey strip, that is, displacing the focus of the camera to a first position where maximally bright bars and minimally bright bars merge as completely as possible to give a homogeneous bright strip where the difference in brightness between the maximally bright bands and minimally bright bands is minimized, which is called a flaw detection position, and keeping the focus at that position. Actual detection of a flaw accompanied with an optical defect consists of checking for the presence of a flag-like image signal.

Although this method allows one to distinguish a flaw accompanied with an optical defect from a simple blemish devoid of optical defect such as a dust or soil, it is impossible by this method to distinguish two different kinds of flaws both accompanied with an optical defect, e.g., to distinguish between a foreign object and an air bubble both entrapped in a test object. The method may include the use of a linearly extended mesh structure, crosswise combined mesh structures obtained by combining two linearly extended mesh structures extending in two directions crossing with each other at right angles, or a checker board patterned mesh structure obtained by arranging light shielding septa and light transmitting slits alternately in rows into a checkerboard pattern. In no matter what pattern the mesh structures may be arranged, one can not distinguish two different kinds of flaws both accompanied with an optical defect in a test object solely dependent on the pattern of light and dark spots obtained from light penetrating the structures: the same flaws may cause different patterns of light and dark spots depending, e.g., on the width of the septa or slits, or on refractions of light incident on them, or two different kinds of flaws may cause the same pattern of light and dark spots. Here, it is appropriate to assume, as an illustration, that there are, in a test transparent plate, a foreign object extending in a direction in which the plate is moved, a second foreign object and an air bubble. The first foreign object may cause a pattern comprising "light, dark, light, dark and light" spots, the second foreign object may cause a pattern comprising "dark, light, dark and light" spots, and the air bubble may cause a pattern comprising "dark, light, dark and light" spots. Thus, one cannot distinguish the three flaws from each other simply dependent on the pattern of dark and light spots carried by light passing through the mesh structure.

DISCLOSURE OF THE INVENTION

One object of the present invention is to provide a testing method by which one can detect a flaw accompanied with an optical defect if any in a sheet-like transparent body in such a manner as to identify the type of the flaw, and a system suitable for executing the method.

Another object of the invention is to provide a testing system with which one can detect a flaw accompanied with an optical defect if any in a sheet-like transparent body as distinct from a dust not accompanied with any optical defect and simply adherent on the surface of the sheet-like transparent body.

A first aspect of the invention is a testing method for detecting a flaw accompanied with an optical defect if any in a sheet-like transparent body which is carried from one place to another. According to this flaw check method, an illuminating means is placed on one side of a test sheet-like transparent body, while a linearly extended (one-dimensional) image pickup means is placed on the opposite side. The illuminating means consists of a lighting portion and darkening portion, and is placed with respect to the image pickup means such that the boundary between the lighting and darkening portions is projected onto the image pickup means as a straight line running essentially in parallel with the latter means, and that the image of the boundary falls on the visual field of the image pickup means. According to this method, a two-dimensional image is reconstructed from one-dimensional outputs provided by the image pickup means; a contrast-enhanced image is produced by subjecting the two-dimensional image to three-value based contrast enhancement, and a flaw is detected and its type is determined based on the pattern of light and dark spots sequentially appearing in the contrast-enhanced image with movement of the test sheet-like transparent body.

A second aspect of the invention is a flaw check system for detecting a flaw accompanied with an optical defect if any in a sheet-like transparent body which is carried from one place to another. The flaw detection system comprises a linearly extending (one-dimensional) image pickup means placed on one side of a test sheet-like transparent body and an illuminating means placed opposite to the image pickup means with respect to the test transparent body. The illuminating means consists of a lighting portion and darkening portion, and is placed with respect to the image pickup means such that the boundary between the lighting and darkening portions is projected onto the image pickup means as a straight line running essentially in parallel with the latter means, and that the image of the boundary falls on the visual field of the image pickup means. The flaw detection system further comprises an image processing device in which a two-dimensional image is reconstructed from one-dimensional outputs provided by the image pickup means, a contrast-enhanced image is produced by subjecting the two-dimensional image to three-value based contrast enhancement, and a sequential pattern (flaw pattern) of light spots and dark spots is traced which appears in the contrast enhanced image with movement of the sheet-like transparent body.

According to the testing method and system of the invention, identification of the type of a flaw is achieved by tracing in what order or in what pattern light spots and dark spots appear or combine when light impinging on a flaw is singularly deflected therewith while a test sheet-like transparent body carrying the flaw moving in one direction, and it is possible thereby to distinguish at least two or more flaws chosen from the group comprising an entrapped foreign object, entrapped air bubble, bump, notch, adhered foreign object, print left by a falling foreign object, etc.

BRIEF DESCRIPTION OF THE DRAWINGS

FIGS. 4A, 4B and 4C illustrate how a flaw consisting of a bump on the surface of a test glass plate is detected and identified.

FIGS. 5A, 5B and 5C illustrate how a flaw consisting of an air bubble entrapped in a test glass plate is detected and identified.

FIG. 6 presents an image obtained from image data derived from a flaw consisting of an entrapped air bubble.

FIG. 7 is a contrast-enhanced image obtained by subjecting the image data derived from a flaw consisting of an entrapped air bubble to three-value based contrast enhancement.

FIG. 9 is a contrast-enhanced image obtained by subjecting the image data derived from a flaw consisting of an entrapped foreign object to three-value based contrast enhancement.

FIG. 11 is a diagram to show how the illuminating means looks like when the system of FIG. 10 is viewed by human naked eyes from its line sensor.

FIGS. 12A, 12B, 12C and 12D illustrate how a flaw consisting of an air bubble entrapped in a test glass plate is detected by the testing system shown in FIG. 10.

FIGS. 14A and 14B show the patterns of "light spots" and "dark spots" representing a falling foreign object and a crater-like print left by a falling foreign object.

FIG. 15 shows the profile of a contrast-enhanced image obtained by subjecting image data representing a dust resting on the surface of a test glass plate to three value based contrast enhancement.

FIG. 16 shows another illuminating means useful for the testing system of the invention.

FIG. 17 shows yet another illuminating means useful for the testing system of the invention.

FIG. 18 shows yet another illuminating means useful for the testing system of the invention.

BEST MODE FOR CARRYING OUT THE INVENTION

Embodiment 1

Figure 1:
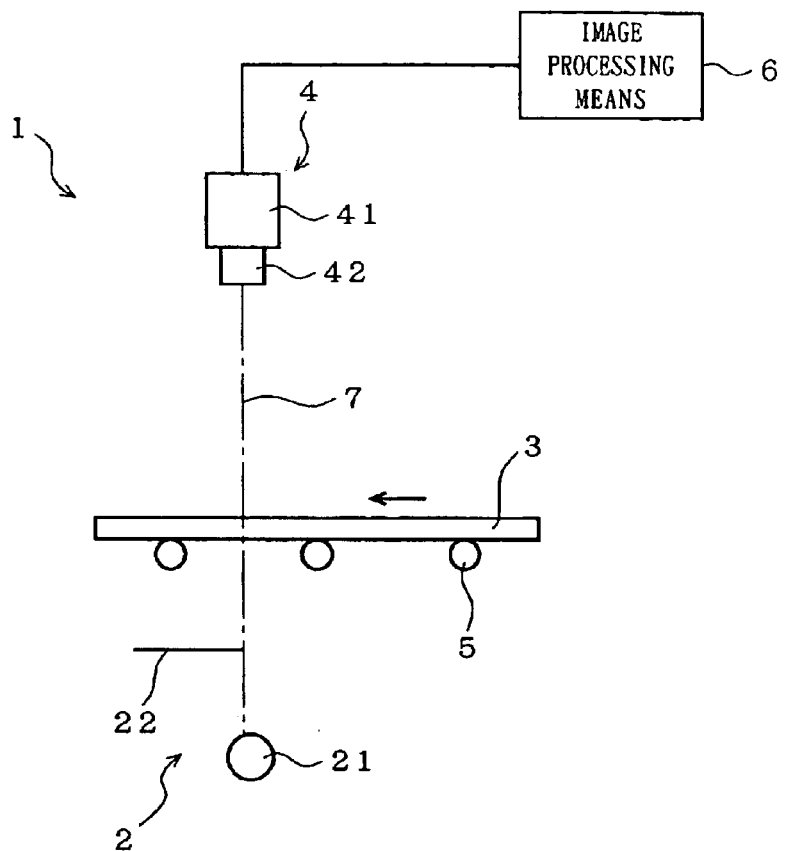
FIG. 1 is a schematic diagram for illustrating the basic composition of a testing system embodying this invention.

FIG. 1 shows the composition of a flaw detection system 1 representing a first embodiment of the invention. The flaw detection system comprises an illuminating means 2, an image pickup means 4, and an image processing means 6. The illuminating means 2 comprises a light shielding plate 22 which forms its darkening portion, and a light source 21 which forms its lighting portion. The image pickup means 4 is a line sensor (resolution being 50 µm) consisting of a sensor beam scanned linearly and repetitively, and comprises a line sensor camera 41 and a lens 42. A test glass plate 3 is moved by a moving means 5 through a space between the illuminating means 2 and image pickup means 4 configured as described above. The direction of the movement is towards left when viewed from front as indicated by the arrow of the figure. One-dimensional output signals from the line sensor 4 are transmitted to the image processing means 6. Based on the one-dimensional output signals, the image processing means 6 produces image data, subjects the image data to three value based contrast enhancement to enhance the contrast of an image represented by the image data, and displays the thus contrast enhanced image comprising "light spots" and "dark spots" the sequential pattern of which indicates the presence of a flaw if any and its type.

The light source 21 or lighting portion of the illuminating means 2 is a straight tubular fluorescent lamp. If the fluorescent lamp is lighted via a power source commercially available, its light intensity will be subject to considerable fluctuations. To avoid this, a high frequency AC power source is used for activating the fluorescent lamp. The driving frequency is set to 30 kHz or higher. Illumination due to a fluorescent lamp activated via a high frequency AC power source is desirable because it requires a low cost and is subject to little fluctuation. Particularly, when a linearly extended light source is required, a straight tubular fluorescent lamp is ideal.

Above the fluorescent lamp 21 is placed the light shielding plate 22 or a darkening portion of the illuminating means 2. The light shielding plate 22 is placed with respect to the line sensor camera 41 such that the edge line of the light shielding plate corresponds with the optical axis 7 of line sensor 4, and that said edge line is placed downstream of the optical axis 7 in terms of the movement of a test glass plate. The light shielding plate 22 is preferably colored black, more preferably matted black, so that its image on the line sensor or a dark strip is sharply contrasted with an adjacent light strip or an image of the light source. To enhance the brightness of the light strip, it is preferable to shift the central axis of fluorescent lamp 21 towards right with respect to the optical axis 7 of line sensor 4 as shown in FIG. 1.

Figure 2:
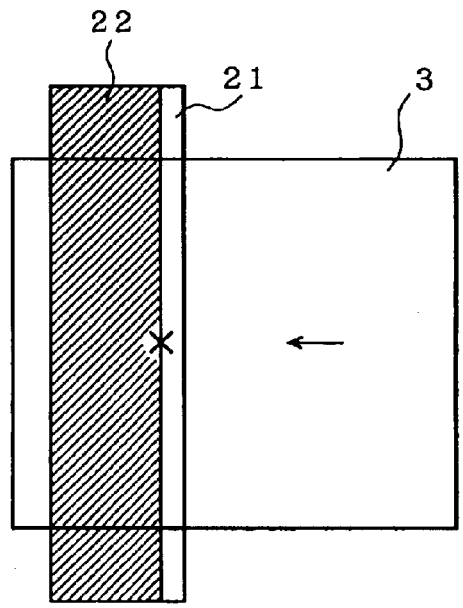
FIG. 2 is a diagram to show how the illuminating means looks like when the system of FIG. 1 is viewed by human naked eyes from its line sensor.

FIG. 2 is a diagram to show how the illuminating means looks like when the system is viewed by human naked eyes from a position close to line sensor 4. The shade of light shielding plate 22 forms a dark strip while light from the lighting surface of fluorescent lamp 21 not intercepted by the light shielding plate 22 forms a light strip. The cross mark at the boundary between the dark and light strips indicates the center of the visual field of line sensor. The line sensor operates by scanning a sensor beam linearly along the boundary between the dark and light strips, and converting the distribution of light intensity along the boundary into corresponding signals.

Above the illuminating means is placed the moving means 5 for moving a test glass plate 3 in one direction. In the particular embodiment shown in FIG. 1, the moving means comprises a set of rollers which rotate so as to move the plate in the direction as indicated by the arrow in the figure. Namely, the moving direction is perpendicular to the direction in which the boundary between the dark and light strips extends.

Above the moving means is placed the line sensor 4 comprising line sensor camera 41 and lens 42. The line sensor camera is placed with respect to the illuminating means 2 such that the boundary between the dark and light strips falls within the visual field of the line sensor camera as described above. The visual field of a line sensor has a certain length, and thus an appropriate number of line sensors may be introduced in the flaw detection system depending on the width of a glass plate to be tested. The line sensor camera 42 is preferably focused close to a test transparent plate, preferably to the surface of a test transparent plate.

The image processing means 6 may include, for embodiment, a computer. If output from the line sensor comprises analog signals, the image processing means 6 should be further provided at least with an image data receiving unit capable of analog/digital (A/D) conversion, i.e., ability to convert analog signals into digital signals, because the computer can handle only digital signals. On the contrary, if the line sensor camera is a digital camera, need for A/D conversion can be safely avoided.

In the following will be described the principle underlying the operation of the flaw detection system, i.e., how the system can detect, when it receives a glass plate 3 with a flaw for inspection, the flaw and determine its type depending on the pattern of "light spots" and "dark spots" reflecting abnormal refractions of light due to the flaw (flaw pattern) which sequentially appear on the screen as the glass plate 3 moves through the system.

Figure 3A:
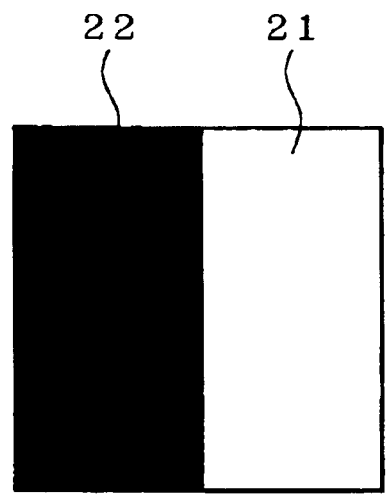
FIGS. 3A and 3B are diagrams to show how the illuminating means look like when viewed by human naked eyes.
Figure 3B:
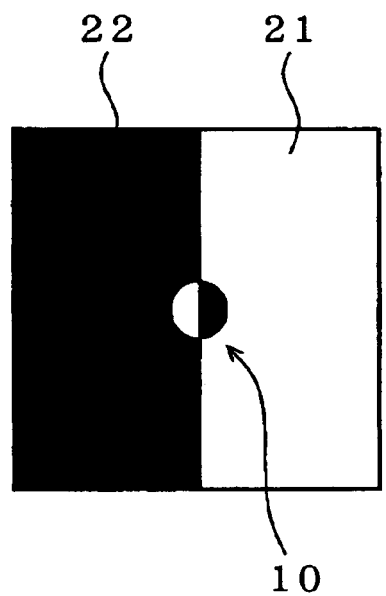

FIG. 1 gives diagrams to show how the illuminating means looks like on the surface of a test glass plate when viewed by human naked eyes placed at the line sensor 4. FIG. 3A shows an image of the illuminating means when the test glass plate has no flaw. The left-side black strip represents the shade of light shielding plate 22 or the darkening portion of the illuminating means, while the right-side white strip represents an image of light source 21 or the lighting portion of the illuminating means. If a glass plate portion carrying a flaw consisting of a bump comes to the boundary between the dark and light strips, light impinging on the bump is refracted so abnormally on account of the convex lens action of the bump that a light spot appears against the dark strip 22 and then a dark spot appears against the light strip 21 as indicated by numeral 10 in FIG. 3B. FIGS. 3A and 3B indicate how the illuminating means looks like when viewed by human naked eyes from a position close to the line sensor. If the same image is viewed by the line sensor which is focused onto the surface of the same glass plate, the boundary between the light and dark strips becomes more blurred, and takes a lightness intensity intermediate between those of the light and dark strips. To let the intermediate light intensity exactly fall at a mid-point between those of the light and dark strips, it is necessary to determine an output from the line sensor after removing the light shielding plate 22, to take the output as 100, and to adjust the position of light shielding plate, when introducing again the light shielding plate into the system, such that an output corresponding with 50 is obtained from the line sensor.

Because the glass plate is constantly moved, the line sensor firstly detects a light spot 21 and then a dark spot 22 occurring as a result of defective refraction due to the bump 10 as described later. Output signals from the line sensor are converted by the image processing means into image data which are then subjected to three value based contrast enhancement to enhance the contrast of an image represented by the image data, and the thus contrast enhanced image comprising "light spots" and "dark spots" is displayed on the screen. It is determined by analyzing the pattern of "light and dark" spots that the flaw includes at least a bump.

A flaw pattern appearing in association with a bump has been described. Next, what pattern of "light and dark" spots appears in association with a notch will be described, together with a pattern appearing in association with an air bubble entrapped in a glass plate.

FIG. 4 illustrates how a flaw consisting of a bump on the surface of a test glass plate is detected and identified as described above with reference to FIGS. 3A and 3B. FIG. 4A illustrates how the line sensor 4 receives light penetrating the front half of bump 31 formed on the surface of glass plate 3 which is moved in one direction. The optical axis of the majority of light impinging on the line sensor 4 is deflected towards the lighting portion of fluorescent lamp 21 from the edge of light shielding plate 22 as a result of the convex lens action of bump 31. Therefore, at this moment, the flux of light impinging on the line sensor becomes larger than that of light penetrating the normal glass plate portion having no such bump.

FIG. 4B illustrates how the line sensor 4 receives light penetrating the rear half of bump 31 formed on the surface of the glass plate which is moved. The optical axis of the majority of light impinging on the line sensor 4 is deflected from the edge of light shielding plate 22 towards the center of the same plate on account of the convex lens action of bump 31. Therefore, at this moment, the flux of light impinging on the line sensor becomes smaller than that of light penetrating the normal glass plate portion having no such bump.

If the system inspects, using the line sensor, a test glass plate having a bump on its surface as described above while the plate is moving, outputs I (representing the light intensity) from the pixels of the line sensor including those receiving light penetrating the bump will give a trace as shown in FIG. 4C. In FIG. 4C, the ordinate represents an output per one pixel of the line sensor, and the abscissa the moving distance L of the glass plate.

In FIG. 4C, the output $I_0$ represents an output per one pixel when the line sensor observes a blurred image of the boundary between the light strip 21 and dark strip 22 as shown in FIG. 3A. However, when an image of a bump comes in the visual field of the line sensor, output from the line sensor becomes higher than the level $I_0$ to give a peak which is followed by a trough smaller than $I_0$.

Outputs from the line sensor are fed via an image data receiving unit to a computer where the outputs are processed to produce image data. Image data are then subjected to three value based contrast enhancement to enhance the contrast of an image represented by the image data, and the thus contrast enhanced image is displayed on the screen. In this case, in correspondence with a bump, there appear on the screen "light spots" and "dark spots" in this order, or a flaw pattern of "light and dark" profile.

Incidentally, it is found that a foreign object entrapped in a glass plate and accompanied with an optical defect causes a flaw pattern of "light and dark" profile as does a bump.

It will be readily appreciated that a notch formed on the surface of a glass plate will generate a contrast enhanced image where "dark spots" and "light spots" appear in this order as opposed to the pattern generated by a bump. A pinhole formed on a glass plate whose surface is coated with a thin film is found to generate a flaw pattern of "dark and light" profile similarly to a notch.

Next, the pattern which will be generated by an air bubble entrapped in a glass plate will be described below. FIG. 5A illustrates how the line sensor 4 receives light penetrating the front half of an air bubble 32 entrapped in a glass plate 3 which is moving. The optical axis of the majority of light impinging on the line sensor 4 is deflected from the edge of light shielding plate 22 towards the center of the same plate on account of the lens action of air bubble. Therefore, at this moment, the flux of light impinging on the line sensor becomes smaller than that of light penetrating the normal glass plate portion having no such air bubble.

FIG. 5B illustrates how the line sensor 4 receives light penetrating the rear half of air bubble 32 entrapped in the glass plate which is moving. The optical axis of the majority of light impinging on the line sensor 4 is deflected towards the lighting portion of fluorescent lamp 21 from the edge of light shielding plate 22 as a result of the lens action of air bubble. Therefore, at this moment, the flux of light impinging on the line sensor becomes larger than that of light penetrating the normal glass plate portion having no such air bubble.

If the system inspects, using the line sensor, a test glass plate entrapping an air bubble as described above while the plate is moving, outputs I from the pixels of the line sensor including those receiving light penetrating the air bubble will give a trace as shown in FIG. 5C. When the air bubble comes to the image of the boundary, output from the line sensor becomes lower than the level $I_0$ to give a trough which is followed by a peak higher than $I_0$. Outputs from the line sensor are fed to a computer where the outputs are processed to produce image data. The image data are then subjected to three value based contrast enhancement to enhance the contrast of an image represented by the image data, and the thus contrast enhanced image is displayed on the screen. In this case, in correspondence with the entrapped air bubble, there appear on the screen "dark spots" and "light spots" in this order, or a flaw pattern of "dark and light" profile.

As described above, the order according to which "light spots" and "dark spots" appear on the screen, that is, flaw pattern of "light and dark" profile observed when a glass plate with a flaw is moved through the flaw detection system, varies depending on the type of the flaw, that is, light deflecting property of the flaw. Therefore, one can determine the type of a given flaw based on the flaw pattern it presents. Identification of the type of a given flaw based on the flaw pattern it presents is hardly possible by using a conventional flaw detection system dependent on a mesh structure comprising plural thin light shielding septa and light transmitting slits as described in the Japanese Examined Patent Publication No. 3178644 as mentioned earlier in "Background Art" section, and is possible only when a flaw detection system as described in this Description is employed which comprises a single light transmitting portion, that is, a single slit instead of plural slits which projects its linear image onto a linearly extended image pickup means in parallel with the long axis of the latter. Incidentally, the actually observed flaw pattern may include such complicated patterns of light and dark spots which may extend in directions other than the direction of movement, that it cannot be ascribed to any specific flaw pattern. Such a complicated flaw pattern, however, may be regarded as derived from a combination of flaws, after it is analyzed into component patterns each ascribable to a different specific pattern.

An illustrative output is presented below when a glass plate entrapping an air bubble is submitted to the flaw detection system. FIG. 6 presents an image displayed on the screen which is obtained by feeding signals from the line sensor 41 via an image signal receiving unit to a computer where the signals are converted into image data which are then transmitted to display without being subjected to any three value based contrast enhancement. The figure also shows vertical and horizontal light intensity profiles along a vertical cursor C1 and horizontal cursor C2. In the figure, the horizontal direction corresponds with the direction of movement of the glass plate while the vertical direction corresponds with the scanning direction of a sensor beam of the line sensor. The distribution of light intensities within the image is so obscure that it cannot be ascribed to any specific flaw pattern of "light spots" and "dark spots."

According to this invention, the computer subjects the two-dimensional image data to three value based contrast enhancement to thereby enhance the contrast of an image represented by the image data. The three value based contrast enhancement consists of firstly determining an average light intensity based on the two-dimensional image data, setting a threshold by a certain amount higher than the average or an over-average threshold, and another threshold by the same amount lower than the average or an under-average threshold using the average as a reference, taking one cluster of image data equal to or larger than the over-average threshold as representing "light spots," another cluster of image data equal to or smaller than the under-average threshold as representing "dark spots," and the rest as representing "grey spots." In the above description, the average is determined based on the entire two-dimensional image data. However, determining the average is not limited to this method. The average may be determined dependent, for embodiment, on the image data derived from light passing through a limited two-dimensional space including a flaw.

A contrast enhanced image obtained by subjecting the aforementioned image data to three value based contrast enhancement is shown in FIG. 7. The distribution of light intensities in the image is more enhanced. It is possible to thereby make a flaw pattern comprising "light spots" and "dark spots" more distinct than a corresponding pattern obtained from the original image data.

From the figure it is obvious that, when an entrapped air bubble is subject to the flaw detection system, firstly "dark spots" appear which are followed by "light spots", that is, a flaw pattern of "dark and light" profile appears with movement of the glass plate. In the particular embodiment shown in FIG. 7, the "light spots" are followed by another group of "dark spots." This may be ascribed to a following phenomenon: if the air bubble is large and optical defect due to the bubble is intense, part of light from the fluorescent lamp to penetrate the bubble is so much deflected that it falls out of the visual field of the line sensor. It is obvious from above that one can detect a small air bubble entrapped in a glass plate based on a flaw pattern of "dark and light" profile, and a large air bubble based on a flaw pattern of "dark, light and dark" profile, with the maximum resolution of the pattern being equal to the resolution of the line sensor or to its n-th multiple.

Figure 8:
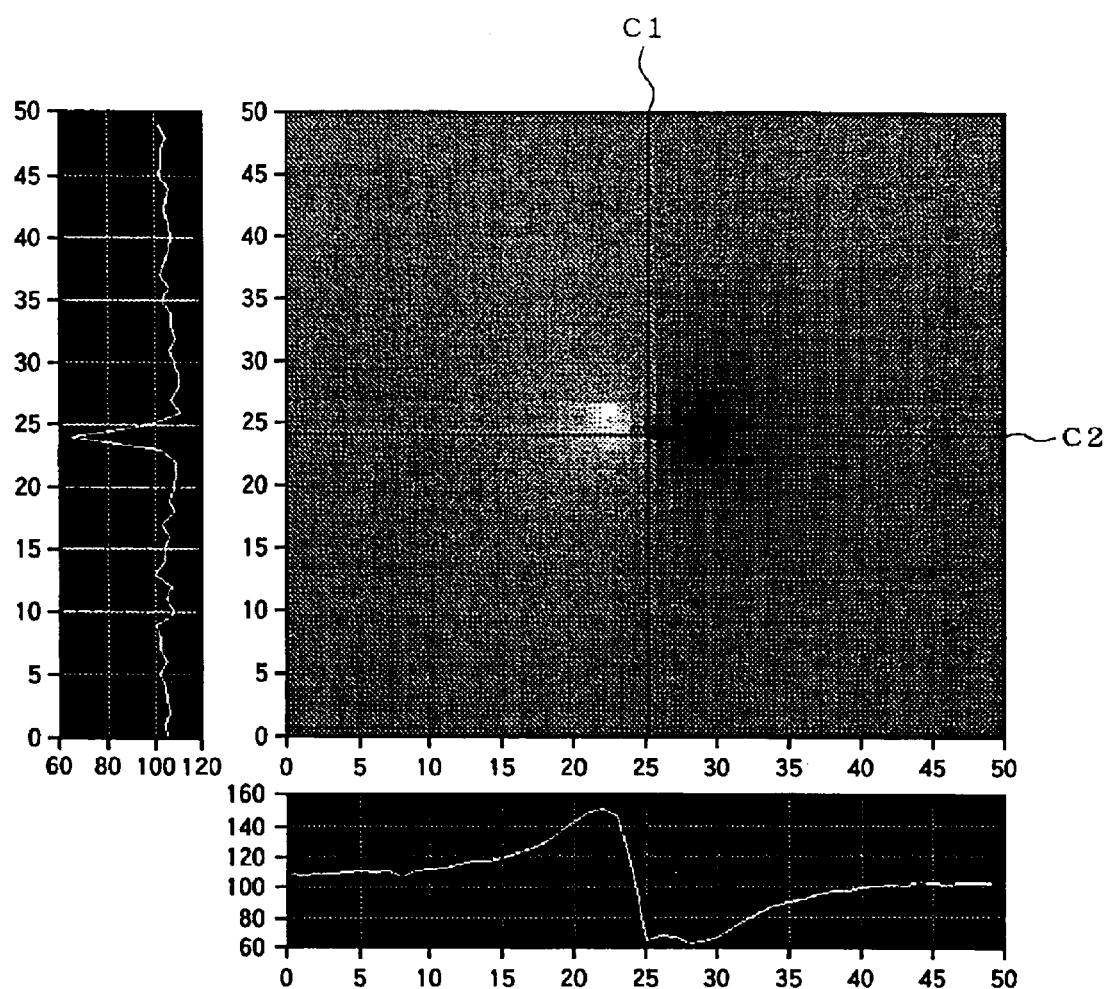
FIG. 8 presents an image obtained from image data derived from a flaw consisting of an entrapped foreign object.

FIG. 8 shows an image obtained from image data prior to contrast enhancement when a glass plate entrapping a foreign object accompanied with a simple bump is applied to the flaw detection system. FIG. 9 shows a contrast enhanced image obtained from the same image data subjected to contrast enhancement. From the figures it is obvious that, when the flaw detection system deals with an entrapped foreign object accompanied with a simple bump, firstly "light spots" appear which are followed by "dark spots", that is, a flaw pattern of "light and dark" profile appears with movement of the glass plate.

As described above, according to the flaw detection system as shown in FIG. 1, it is possible to distinguish at least between an entrapped air bubble and an entrapped foreign object based on the flaw patterns they present.

It will be readily obvious to those skilled in the art that, according to the flaw detection system shown in FIG. 1, when the moving direction of a test glass plate 3 with a flaw is reversed, the order in which light and dark spots appear with movement of the glass plate is reversed to the initially observed order.

Embodiment 2

Figure 10:
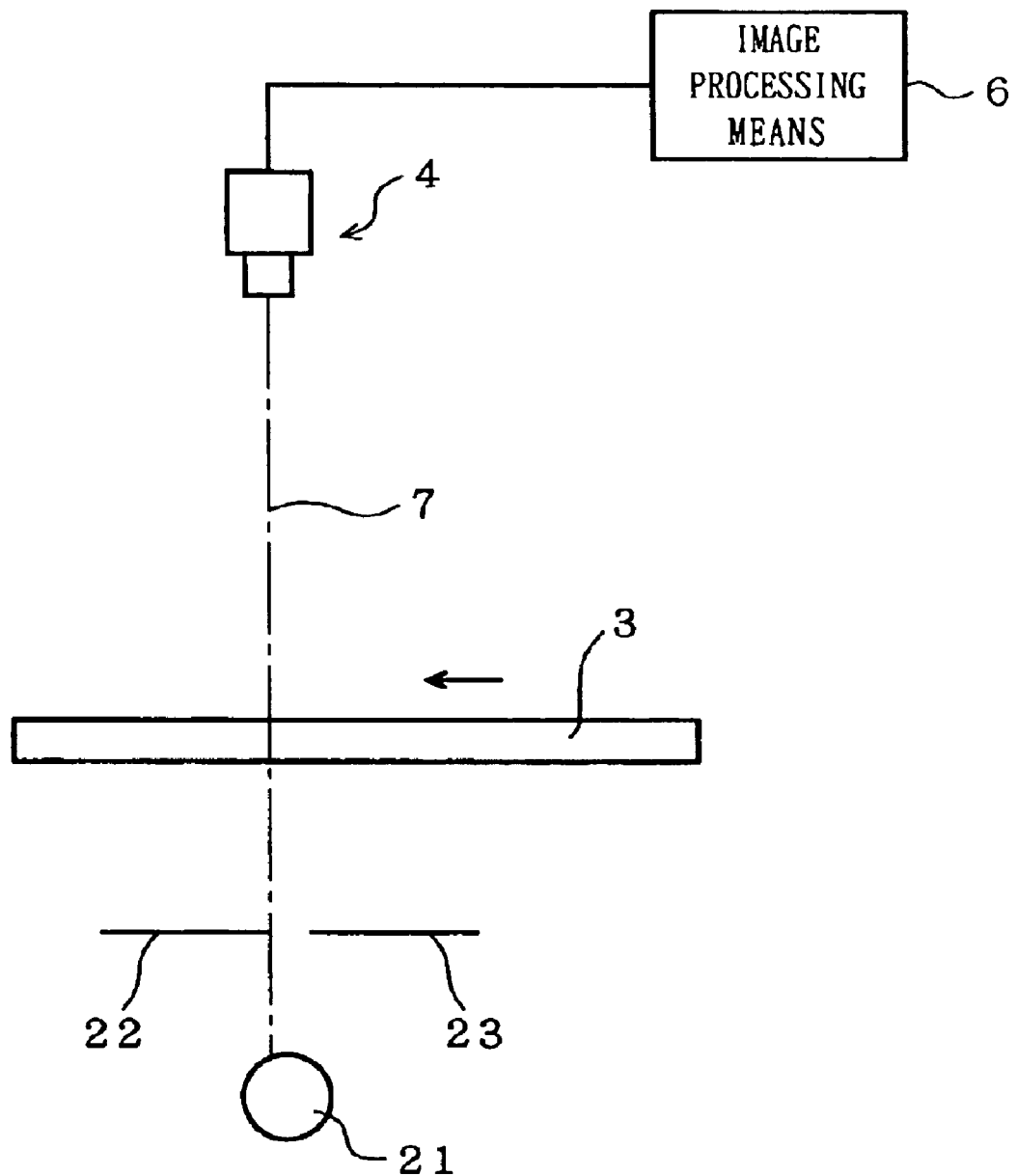
FIG. 10 shows another testing system to which a second light shielding plate is added.

The flaw detection system described above as Embodiment 1 incorporates a light shielding plate 22 consisting of a single plate. The flaw detection system of this embodiment incorporates instead a light shielding plate including an additional plate. FIG. 10 shows the flaw detection system representing Embodiment 2. A second plate 23 added to the light shielding plate is introduced so as to intercept scattered light which as a background light, out of light from a fluorescent lamp 21, and to thereby reduce light diffusely reflected by a flaw. The additional light shielding plate 23 may be adjusted in its position in as much as it does not encroach on the visual field of the line sensor.

FIG. 11 is a diagram to show how the illuminating means looks like when the system of FIG. 10 is viewed by human naked eyes from its line sensor 4. The two light shielding plates 22, 23 appear dark strips while the lighting surface of the fluorescent lamp 21 which is not masked by the two light shielding plates appears as a light strip 21. The cross-placed at the boundary between the light strip 21 and dark strip 22 marks the visual center of the line sensor.

Here, it is appropriate to consider the case where this system is applied for detecting a large air bubble entrapped in a glass plate by following the pattern of light and dark spots generated by the bubble with movement of the glass plate, with the maximum resolution of spot detection being equal to the resolution of the line sensor or to its n-th multiple. Then, a series of "dark spots," "light spots" and "dark spots" or a flaw pattern of "dark, light and dark" profile as shown in FIG. 6 will be most frequently observed. FIGS. 12A, 12B and 12C, and 12D show illustrations corresponding with those of FIGS. 5A and 5B, and 5C, respectively. They illustrate how a flaw pattern of "dark, light and dark" profile is obtained from a large air bubble entrapped in a glass plate with movement of the glass plate. In FIG. 12A, the line sensor receives light penetrating the front part of the air bubble entrapped in the glass plate, and the intensity of light then received by the line sensor is lower than $I_0$ as indicated by a first trough in FIG. 12D. In FIG. 12B, the line sensor receives light penetrating a descending shoulder of the air bubble, and the intensity of light then received by the line sensor is slightly higher than $I_0$. In FIG. 12C, the line sensor receives light penetrating the trail of the air bubble, and the intensity of light then received by the line sensor is again lower than $I_0$.

Then, how the flaw detection system detects a foreign object falling from above and adhering to the surface of a glass plate, or a crater-like print left by such a falling object will be described.

Figure 13A:
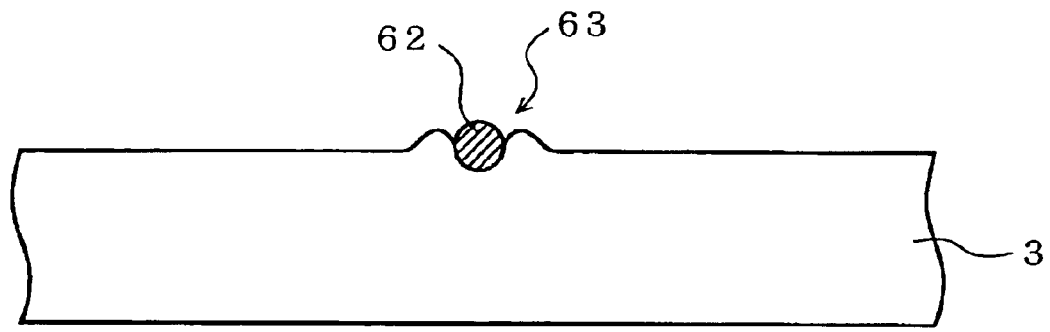
FIGS. 13A and 13B show the profiles of two flaws: one consists of a falling foreign object on the surface of a test glass plate, and the other of a crater-like flaw consisting of a central pit and surrounding edge left by such a falling foreign object.
Figure 13B:
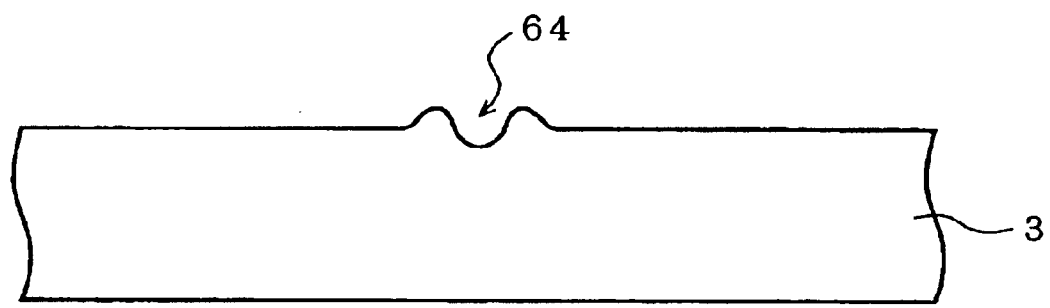

FIGS. 13A and 13B show the profiles of two flaws: one consists of a falling foreign object on the surface of a test glass plate accompanied with an annular ridge, and the other of a crater-like pit and surrounding ridge left by such a falling foreign object. As shown in FIG. 13A, a flaw 63 resulting from a foreign projectile 62 striking the surface of a glass plate is surrounded with an annular ridge, and image data obtained from this flaw, when subjected to contrast enhancement, gives a flaw pattern of "light and dark" profile similar to that of a flaw consisting of a bump. An exemplary flaw pattern of "light and dark" profile as described above is shown in FIG. 14A. A crater-like print 64 left by a falling foreign object as shown in FIG. 13B gives, when the image data is contrast-enhanced, a flaw pattern of "light, dark, light and dark" profile as shown in FIG. 14B. It is found that a print left by a small foreign object gives a flaw pattern of "light and dark" profile with the maximum resolution being equal to the resolution of the line sensor or its n-th multiple.

Next, with the flaw detection system as shown in FIG. 10, the line sensor is focused onto the surface of a glass plate, a dust on the surface is traced, a contrast-enhanced image thereof is displayed on the screen, and the profile of a flaw pattern obtained from the image is shown in FIG. 15. As is obvious from inspection of the figure, a dust only generates "dark spots." This is because a dust only intercepts the entry of light which reduces the intensity of light incident on the line sensor and causes dark spots to appear.

Accordingly with the flaw detection system where the line sensor is focused onto the surface of a test glass plate, and introduction of an additional light shielding plate 23 restricts the entry of scattered light, it is possible to distinguish between a flaw accompanied with an optical defect and a simple blemish such as a dust devoid of optical defect by analyzing respective sequential patterns of "light spots" and "dark spots" observed in their contrast-enhanced images.

It will be readily obvious to those skilled in the art that, according to the flaw detection system shown in FIG. 10, when the moving direction of a test glass plate 3 with a flaw is reversed, the order in which light and dark spots appear with movement of the glass plate is reversed to the initially observed order.

The dust includes debris which is generated while a master glass plate is cut into elementary glass plates and which may adhere to the surface of elementary glass plates as a foreign object. Since such debris, when receiving light, deflects it so abnormally that it is possible to detect a flaw caused by it by analyzing the optical defect associated with it like other flaws accompanied with an optical defect. However, debris generated as a result of cutting a master glass plate may often cause a complicated flaw pattern comprising "light spots" and/or "dark spots."

With Embodiments 1 and 2, an image of the boundary between the lighting portion and darkening portion of the illuminating means 2 runs in a direction perpendicular to the direction in which a test transparent plate is moving. However, the angle between the two directions may not be an exact rectangle but close to a rectangle. If it is desired to particularly detect a flaw which has a direction corresponding to the direction in which a glass melt is allowed to flow prior to the formation of a plate, the angle between the moving direction of the glass plate and the direction of the visual field of the line sensor may be adjusted as appropriate so that the flaw detection system can best detect such a flaw.

Variant Embodiments

Although the flaw detection system of Embodiment 1 comprises an illuminating means which consists of a fluorescent lamp and a light shielding plate, the system configuration is not limited to this. For embodiment, the single fluorescent lamp may be substituted for two fluorescent lamps 21 as shown in FIG. 16.

Alternatively, the illuminating means may comprise a plurality of fluorescent lamps 21 and a light shielding plate 24 and light scattering plate 25 placed above the lamps as shown in FIG. 17.

With the embodiments and variant embodiments mentioned above, the light source consists of one or plural fluorescent lamp(s). However, the light source may include, in addition to a fluorescent lamp(s), for embodiment, a halogen lamp(s). Namely, light guided by plural optical fibers from a halogen lamp(s) may be used as a light source. Furthermore, the light source may include a rod-like LED.

The transparent plate to which the flaw detection system of the invention is applied is not limited to those in which the surfaces are uniformly flat and run in parallel. The plate may include those that have a gentle curvature like a display panel. The plate may further include plate strips having a moderate length, or long continuous plate strips. The flaw detection system of the invention is also applicable to semi-transparent plates, as long as they are capable of transmitting light.

INDUSTRIAL APPLICABILITY

As detailed above, according to the testing method and system of the invention, it is possible to detect a flaw accompanied with an optical defect if any on or in a glass plate, by analyzing a pattern observed in its contrast-enhanced image comprising "light spots" and "dark spots." Particularly, it is possible to determine the type of the flaw by following the order in which "light spots" and "dark spots" appear with movement of the glass plate, and how "light spots" and "dark spots" combine.

According to the testing method and system of the invention, it is also possible to detect a flaw not accompanied with any optical defect such as a simple blemish like a dust adherent on the surface of a glass plate which can be removed. Thus, it is possible according to the testing method and system of the invention to distinguish a flaw consisting of a simple blemish from a flaw consisting of a bump or notch formed on the surface, or of a foreign object or air bubble entrapped in the glass plate, and to separately treat glass plates having the former flaw from those having the latter flaw. By virtue of this, the flaw detection method and system of the invention does not necessarily require, for the test, a clean space as provided by a clean booth or the like, which will help to reduce costs. Moreover, according to the method and system of the invention, it is also possible to acquire information about what kind of handling causes frequent adherence of dusts on the surface of glass plates. This information enables one to improve the polishing process in the manufacture of glass plates.

What is claimed is:

1. A flaw detection system for detecting a flaw accompanied with an optical defect if any on or in a sheet-like transparent body which is moved, comprising:

a linearly extended (one-dimensional) image pickup means placed on one side of the sheet-like transparent body:

an illuminating means placed on the opposite side of the sheet-like transparent body, the illuminating means comprising a lighting portion and a darkening portion, the lighting and darkening portions of the illuminating means being constituted respectively with a light source, a first light shielding plate which is placed between the light source and sheet-like transparent body to shield part of the light source such that an image of the edge of the first light shielding plate forms a visual field of the image pickup means, and a second light shielding plate is placed between the illuminating means and sheet-like transparent body so as to intercept scattered light which is a background light, out of light from the light source to thereby reduce light diffusely reflected by a flaw; and an image processing means in which two-dimensional image data are created from one-dimensional output from the image pickup means, the image data are subjected to three value based contrast enhancement to convert said data into contrast enhanced image data which are then utilized to display a contrast enhanced image, the sequential pattern (flaw pattern) of light spots and dark spots is traced which appears in the contrast enhanced image with movement of the sheet-like transparent body.

2. A flaw detection system according to claim 1, wherein identification of the type of a flaw is achieved by determining the sequential order in which light spots and dark spots constituting the flaw pattern appear with movement of a sheet-like transparent body or the combination of light spots and dark spots in the flaw pattern.

3. A flaw detection system according to claim 2, wherein the types of flaws to be distinctly identified comprise at least a flaw consisting of a foreign object and a flaw consisting of an air bubble.

4. A flaw detection method according to claim 2, wherein the types of flaws to be distinctly identified comprise at least one chosen from the group comprising flaws consisting of a foreign object, air bubble, bump, notch, falling foreign object, and print left by a falling foreign object.

5. A flaw detection system according to claim 1, wherein the linearly extended (one-dimensional) image pickup means brings its focus close to a sheet-like transparent body; and when a "dark" pattern appears in a contrast enhanced image, the system determines that the flaw responsible for the "dark" pattern is a dust adherent on the surface of the sheet-like transparent body.

6. A flaw detection system according to claim 1, wherein the sheet-like transparent body comprises a glass plate.

7. A flaw detections system according to claim 1, wherein the sheet-like transparent body comprises a glass plate whose surface is coated with a transparent film.

8. A flaw detection system according to claim 7, wherein the type of flaw to be identified further comprises a pinhole if any present in the transparent film.

* * * * *